United States Patent [19]
Mikkelsen

[11] Patent Number: 5,611,783
[45] Date of Patent: Mar. 18, 1997

[54] PEN-SHAPED SYRINGE

[75] Inventor: Søren Mikkelsen, Ballerup, Denmark

[73] Assignee: Novo Nordisk A/S, Bagsvaerd, Denmark

[21] Appl. No.: 256,888

[22] PCT Filed: Nov. 30, 1992

[86] PCT No.: PCT/DK92/00359

§ 371 Date: May 20, 1994

§ 102(e) Date: May 20, 1994

[87] PCT Pub. No.: WO93/10839

PCT Pub. Date: Jun. 10, 1993

[30] Foreign Application Priority Data

Nov. 29, 1991 [DK] Denmark ................................. 1942/91

[51] Int. Cl.[6] .................................................. A61M 5/00
[52] U.S. Cl. ........................... 604/208; 604/211; 604/218
[58] Field of Search ......................... 604/208–211, 220, 604/201, 71, 72, 135, 136, 224, 218, 287, 232, 207

[56] References Cited

U.S. PATENT DOCUMENTS 1,595,424  8/1926  Sather .
4,865,591  9/1989  Sams .................................. 604/209
4,936,833  6/1990  Sams .................................. 604/209
4,973,318  11/1990 Holm et al. ......................... 604/208
5,226,895  7/1993  Harris ................................. 604/211
5,304,152  4/1994  Sams .................................. 604/208

FOREIGN PATENT DOCUMENTS 675078  8/1990  Switzerland .

Primary Examiner—Corrine M. McDermott
Assistant Examiner—Ronald K. Stright, Jr.
Attorney, Agent, or Firm—Steve T. Zelson, Esq.; James Harrington, Esq.

[57] ABSTRACT

A pen-shaped syringe comprises a first part containing a dose setting and driving mechanism from which a piston rod is advanced by a carrier to actuate a piston of a reservoir in a second part. The first and second parts are coupled together by a bayonet coupling, wherein the bayonet coupling element of the second part has members for rotating a piston rod guide mounted on the bayonet coupling element of the first part. The piston rod determines the rotational position of the piston rod which rotational position again determines the engagement between the carrier and the piston rod.

5 Claims, 2 Drawing Sheets

PEN-SHAPED SYRINGE

BACKGROUND OF THE INVENTION

The invention relates to pen shaped syringes comprising a proximal part containing a dose setting and driving mechanism, a piston rod having a non-circular cross section and carrying along one side a cogging engaged by a carrier unidirectonally transmitting axial movements from the driving mechanism to the piston rod, a piston rod guide positioned to maintain the piston rod in a rotational position in the syringe ensuring the engagement between the carrier of the drive mechanism and the cogging of the piston rod, the piston rod guide having a non-circular opening conforming to the cross section of the piston rod, and through which opening the piston rod passes, and a distal part containing a tubular reservoir for medicine, which reservoir at its distal end is closed by a pierceable rubber membrane, and at its proximal end is closed by a piston actuated by the piston rod of the proximal part.

DESCRIPTION OF RELATED ART

Such syringes are used by patients which have to frequently inject themselves. The reservoir contains medicine sufficient for several injections, and when the reservoir is empty, the proximal and the distal part of the syringe may be unscrewed and the reservoir renewed, whereafter the parts are screwed together again.

However, this screwing movement may be difficult to perform especially to patients suffering from diseases reducing their tactile motor function, and this way it may be difficult for these patients to administer the medicine which could just mitigate these symptoms.

SUMMARY OF THE INVENTION

Therefore, it is the object of the invention to provide a pen syringe wherein the medicine reservoir could easily be changed without performing many turns of screwing.

This is obtained by a syringe of the above mentioned kind, which syringe according to the invention is characterized in, that the proximal and the distal part have interlocking bayonet coupling means, and that the bayonet coupling means on the distal part is provided with means engaging the piston guide to rotate this guide and consequently the piston rod during at least part of the rotational movement of the bayonet lock.

When a reservoir is emptied the piston rod is protruding from the proximal part, and the engagement between the piston rod and the drive mechanism has the effect that the piston rod may not immediately be pushed back into the proximal part to be ready for actuating the piston of a new full reservoir. Therefore, a coupling is normally provided to release the engagement between drive mechanism and piston rod when the pen is unscrewed. This coupling is normally operated to reestablish the engagement when the parts are screwed together again, the operation being performed by the reservoir pressing a coupling member when the distal part is screwed onto the proximal part. This arrangement has the disadvantage that the coupling is performed before the parts are screwed totally home, and consequently, if the piston rod is pushed back by the piston of the new reservoir, the movement of the piston rod will be locked and will press the piston into the reservoir during the last part of the screwing. By the pen syringe according to the invention the coupling is performed by rotating the piston rod out of and into is engagement with the drive mechanism, and as this rotation is Performed without any concomitant axial movement the above mentioned disadvantage is avoided.

According to the invention, the bayonet coupling may comprise a stud protruding from a plane distal end surface of the proximal part, this stud being provided with a flange having an outer diameter corresponding to the inner diameter of the tubular distal part and leaving a space between the flange and the end surface, the flange being cut away preferably at diametrically opposite positions, and locking protrusions on the inner surface at the proximal end of the distal part, which protrusions correspond to the cuts of the flange and extend in the axial direction from the proximal end of the distal part to a position a distance away from this proximal end, which distance corresponds to the distance between the flange and the end surface.

According to the invention, the piston guide may be mounted at the distal end of the stud rotatably journaled in this stud and having a disc with a diameter corresponding to the diameter of the flange and with cuts at least corresponding to the cuts of the flange, the flange and the disc being provided with engaging stop means limiting the rotational movement of the piston guide, and the inner surface of the distal part may be provided with a protrusion engaging a cut in the piston guide disc, which protrusion lies at a distance from the proximal end of the distal part corresponding to the length of the stud.

The bayonet lock may be provided by the flange being provided with a set of cuts comprising a first cut forming a slot through the flange and a pair of cuts at a position principally diametrically opposite the first cut, but provided on both sides of a piece of the flange left at the position exactly diametrically opposite the first cut. This arrangement allows a 180° turning to lock the bayonet lock, as the protrusion passed through the first cut will abut the rear side of the left piece of the flange, and protrusions corresponding to the pair of cuts will abut the rear side of the flange on both sides of the first cut.

The distal part of the syringe may be manufactured as an integral disposable part containing the reservoir and a pawl mechanism for engagement with the cogging of the piston rod, and the cut in the piston guide disc engaged by a protrusion on the inner side of the distal part of the syringe may extend over an arch of 90°. As the pawl mechanism, which forms a retraction detent for the piston rod during the use of the syringe, is a part exposed to heavy wear it is appropriate to make this part disposable, so that it is changed each time a new reservoir is mounted.

By making the cut in the piston drive disc span 90°, the piston rod is maintained unrotated during the first 90° of the turning of the distal part, and this part of the turning may be used to bring the pawl mechanism in this distal part into engagement with the cogging of the piston rod. When the disc engaging protrusion of the distal part reaches the end of the arched cut in the disk, this disc and consequently the piston rod are rotated during the last 90° of the turning of the distal part and may this way come into engagement with the drive mechanism in the proximal part of the syringe.

The piston rod may appropriately have a square cross section and be provided with coggings along two opposite sides and be smooth along the other two opposite sides.

In the following the invention is described with reference to the drawing wherein

DESCRIPTION OF THE PREFERRED EMBODIMENTS

Figure 1:
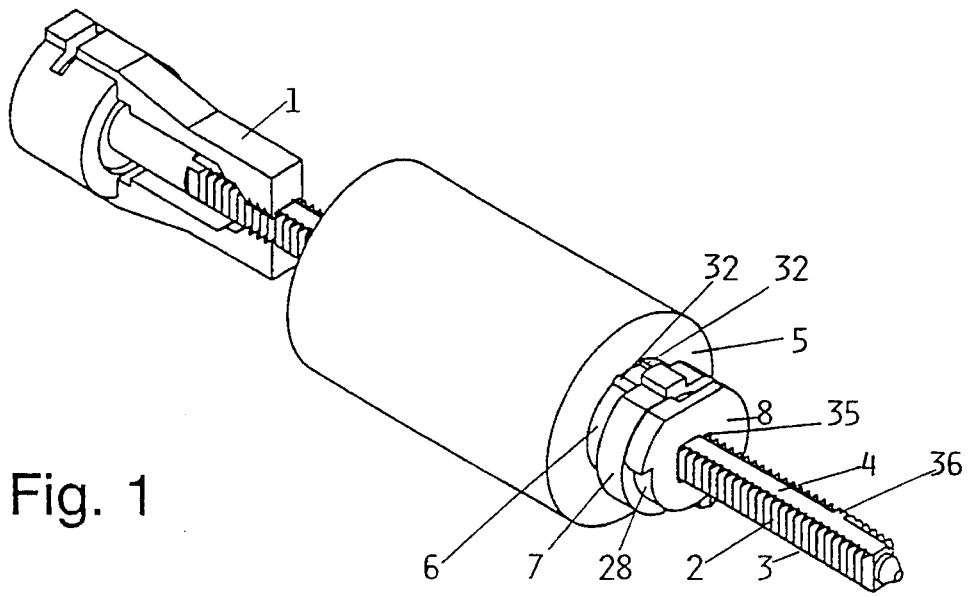
FIG. 1 shows the distal end of a proximal part of a pen syringe with a bayonet coupling according to the invention, the piston guide being in an initial rotational position.

FIG. 1 shows the distal end of the proximal part of a pen shaped syringe, which proximal part comprises not shown elements for setting a dose which is injected by advancing a carrier 1 having teeth for engagement with the coggings 2 along two opposite sides of a piston rod 3 having a square cross section, the other pair of opposite sides 4 being smooth. The teeth of the coggings have a steep leading edge and a ramp shaped rear edge to ensure a unidirectional advancing of the piston rod when the carrier 1 is reciprocated during consecutive injections.

Figure 2:
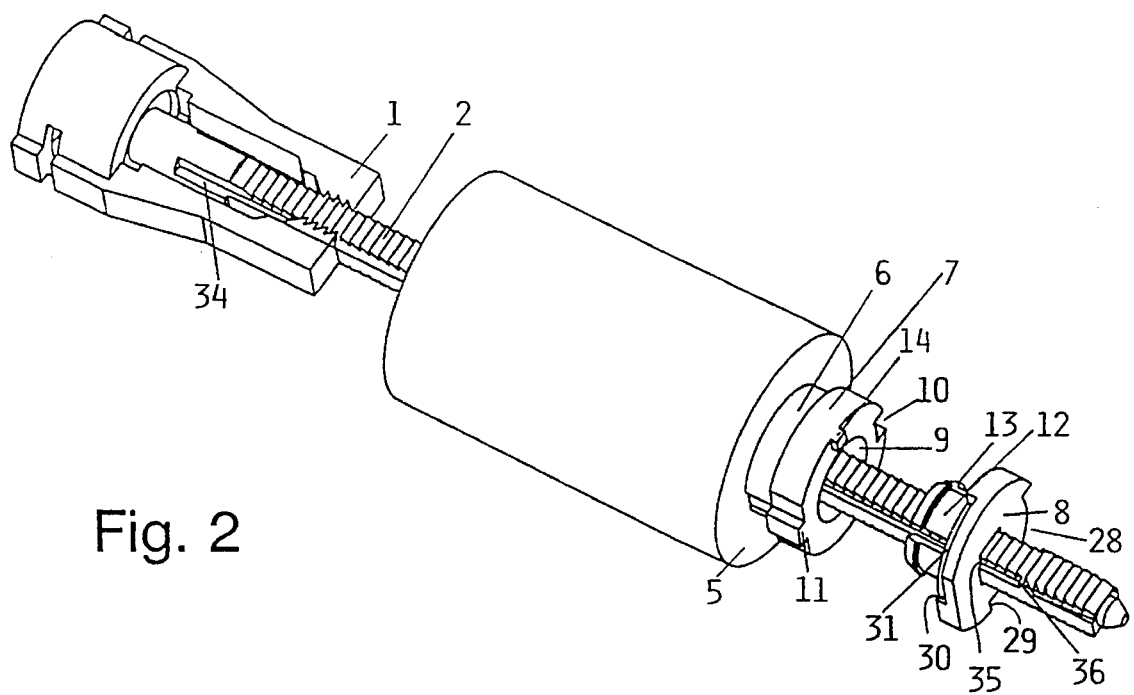
FIG. 2 shows the same part of the syringe as FIG. 1 with the piston guide drawn away from the bayonet coupling, the piston rod guide being in the initial rotational position.
Figure 3:
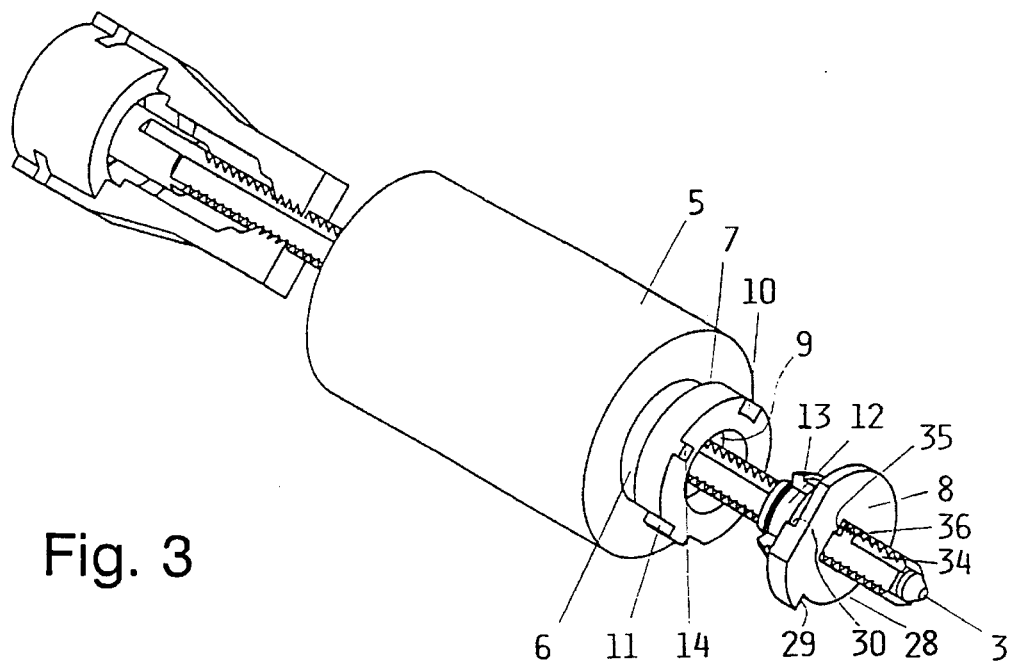
FIG. 3 shows the same part of the syringe as FIG. 2 with the piston guide drawn away from the bayonet coupling, the piston rod guide being in a final rotational position.

The part shown in FIG. 1 is terminated by a plane end surface 5 carrying a bayonet coupling part comprising a tubular stud 6 with a flange 7. A piston rod guiding disc 8 is rotatably mounted to the stud 6 at the outer end of the flange. As illustrated in FIG. 2, wherein the disc is shown drawn away from the flange, this mounting is obtained by the disc 8 being provided with a tubular projection 12 on the side facing the flange, which projection is terminated by a snap lock hook 13 gripping behind an inner shoulder when the projection 12 is inserted in a central bore 9 through the stud.

The piston rod 3 passes through an opening in the disc 8, which opening conforms to the cross section of the piston rod 3 to keep this piston rod in a rotary position defined by the rotary position of the disc 8. In the initial position shown in FIGS. 1 and 2, the piston rod is maintained in a rotational position causing the teeth of the carrier 1 to rest on the smooth sides of the piston rod 8 the carrier being unrotatable in the proximal part of the syringe. In this position the piston rod may be pushed back into the proximal part, as its smooth sides may slide between the jaws of the carrier 1.

The piston rod 3 having a substantially square cross section has along two of its edges recesses 34 corresponding to protrusions 35 on the wall of the opening in the disk 8, the protrusions 35 projecting into this opening. Near the distal end of the piston rod the recesses 34 are interrupted by protrusions 36 provided by the pisron rod having its full square cross section. As due to the protrusions 35 the protrusion 36 cannot pass through the opening in the disc 8 a stop is provided for the movement of the piston rod into the proximal part.

The flange 7 is at its periphery provided with a recess 10 in the axial direction of the stud, and at a position diametrically opposite the recess 10 cuts in the flange make the remaining part of the flange appear as a projection 11 diametrically opposite the recess 10. Further, a protrusion 14 on the end surface of the flange projects into a 90° arched recess along the periphery of the disc 8.

Figure 4:
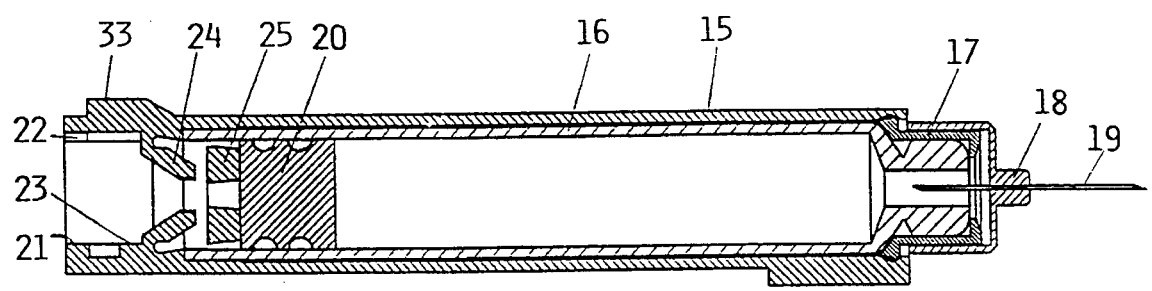
FIG. 4 shows a sectional view of a distal part of the syringe, this distal part comprising a reservoir and a bayonet coupling part for engagement with the mating bayonet coupling part on the distal end of the proximal part of the syringe.
Figure 5:
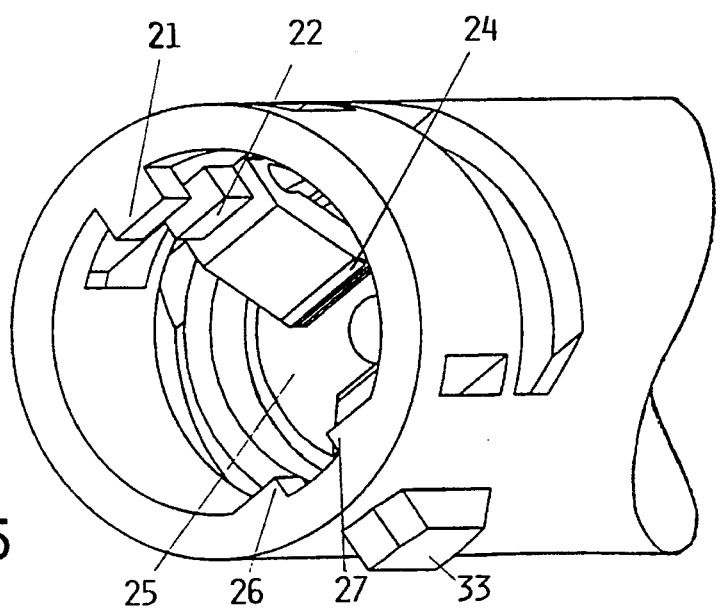
FIG. 5 shows in an enlarged scale the coupling part at the proximal end of the distal part of the syringe.

The stud 6 and the flange 7 with its recess 10 and its projection 11 form one half of a bayonet coupling, the other half being provided at a proximal end of a distal part of the syringe as shown in FIG. 4 and in further details in FIG. 5.

FIG. 4 shows a sectional view of the distal part comprising a housing containing a cylinder ampoule 16. At its distal end the housing 15 is provided with a threaded member 17 receiving a hub 18 with a hypodermic needle 19 communicating with the internal space of the ampoule which is at its proximal end closed by a piston 20 which may be forced into the ampoule to press out its content through the needle 19. The proximal end of the housing has on its inner wall a coupling protrusion 21, a coupling recess 22, and a disc drive protrusion 23, which protrusions are designed for cooperation with the bayonet coupling part of the proximal part of the syringe.

When the distal part of the syringe is mounted on the proximal part which is in the position shown in FIGS. 1 and 2, the coupling protrusion 21 is passed into the recess 10 in the flange 7, and the projection 11 of the flange is passed into the coupling recess 22 formed between two internal protrusion 26 and 27 at the proximal end of the tubular housing 15. The disc 8 is provided with a 90° arched cut allowing the protrusion to pass the disc which else covers the end surface of the flange 7. During this operation the piston rod is pushed back into the proximal part until the projections 36 in the recess 34 in the piston rod 3 abut the projections 35 in the opening of the disc 8 and prevent a further movement of the piston rod 3. The end of the piston rod projecting from the proximal part will then be pressed into the space between the withdrawal detent pawl jaws 24, and these jaws to will slide along the smooth sides of the piston rod which is moved into the distal part towards a piston foot 25. When the proximal edge of the distal part abuts the end surface 5 of the proximal part of the syringe, the distal part is turned clockwise relatively to the proximal part. By this rotation the protrusion 21 will pass into the clearance between the surface 5 and the flange 7, and the flange will be adopted in the clearance between the protrusions 21 and 23 and behind the protrusions 26 and 27.

During the first 90° of the relative rotation the protrusion 23 will follow an arched 90° cut 28 in the disc 8, and consequently the piston rod will maintain its rotational position, i.e. the distal part will be rotated relatively to the piston rod. When the distal part is rotated 90°, the jaws 24 of the retraction detent will come into engagement with the cogging of the piston rod 3. Further, the disc drive protrusion 23 will abut the terminal surface 29 of the cut 28, and a continued rotation will be transmitted to the disc 8 and consequently to the piston rod, i.e. the piston rod 3 will now be rotated with respect to the proximal part of the syringe but not with respect to the distal part. By further clockwise turning of the distal part in relation to the proximal part, the jaws 24 will remain in engagement with the coggings of the piston rod, and a 90° further rotation will bring the carrier 1 into engagement with these coggings. The protrusion 21 will then be lodged behind the protrusion 11, and the protrusions 26 and 27 will be lodged at respective sides of the recess 10. Further relative rotation of the proximal and distal parts is obstructed partly by the protrusion 14 on the end surface of the flange abutting the terminal surface 30 of the arched recess 31 of the disc and partly by the protrusion 21 being adopted between two ridges 32 provided on the cylindric surface of the stud 6.

When the reservoir is empty, the parts may be dismounted by turning the distal part 180° anticlockwise in relation to the proximal part.

In the distal part some openings and cuts only serving moulding purposes are seen.

An external protrusion 33 at the proximal end of the distal part may be provided to engage a recess in a not shown housing of the proximal part to ensure that the two parts are placed in the correct mutual rotational position to be coupled together. More similar protrusions may be provided to form a pattern ensuring that a certain distal part may only be used in connection with a certain proximal part. The distal part is shown as a housing containing a cylinder ampoule, but it may also be an integral part.

In a not shown embodiment the withdrawal detent jaws may be placed in the proximal part. Then only a 90° relative rotation of the distal part with respect is to the proximal part is necessary to make the teeth of the carrier as well as the teeth of the withdrawal detent engage the coggings of the piston rod. When only a 90° relative rotation is needed, the bayonet coupling may be made more simple with only recesses in the flange and only protrusions on the inner wall of the distal part.

I claim:

1. An apparatus for use with a pen shaped syringe comprising a first part having an end surface carrying a tubular stud with a flange forming a bayonet coupling part, and a second part having interlocking bayonet coupling means for engagement with the bayonet coupling part of the first part, the first part further comprising:

(a) a piston rod projecting through the stud and having a non-circular cross section and carrying along one side a cogging, (b) a carrier on a proximal end of the piston rod which can be advanced to inject a set dose of medicine and which unidirectionally transmits axial movements of this carrier to the piston rod, (c) a piston rod guide mounted on the stud at an end of the flange, said piston rod guide maintaining the piston rod in a rotational position in the syringe ensuring the engagement between the carrier and the cogging of the piston rod when the syringe is in use, the piston rod guide having a non circular opening conforming to the cross section of the piston rod, and through which opening the piston rod passes, said second part being tubular and having an open proximal and a distal end, said interlocking bayonet coupling means being on said proximal end thereof, the second part further comprising:

(a) a tubular reservoir for medicine, located within said second part which reservoir has a first end placed at the distal end of the second part, and a second end placed at the proximal end of the second part and closed by a piston which can be actuated by the piston rod, wherein the interlocking bayonet coupling means of the second part is provided with means engaging the piston rod guide to rotate this guide and consequently the piston rod during at least part of a rotational movement of the bayonet coupling means in relation to the stud, the flange having an outer diameter corresponding to an inner diameter at the proximal end of the tubular second part, such that a space is left between the flange and the end surface of the first part, the flange being cut away preferably at diametrically opposite positions, and locking protrusions on an inner surface of the proximal end of the first part corresponds to the cut of the flange and extend axially from the proximal end a distance way from this proximal end, which distance corresponds to the distance between the flange and the end surface of the first part.

2. An apparatus according to claim 1, wherein the piston rod guide has the shape of a piston rod guide disk, which has a diameter corresponding to the diameter of the flange, and which piston rod guide disk has cuts at least corresponding to the cuts of the flange, the flange and the piston rod guide disk being provided with engaging stop means limiting the rotational movement of the piston rod guide disk, and an inner surface of the second part is provided with a protrusion engaging a cut in the piston rod guide disk, which protrusion lies at a distance from the proximal end of the second part corresponding to the length of the stud.

3. An apparatus according to claim 2, wherein the second part of the syringe further comprises an integral pawl mechanism for engagement with the cogging of the piston rod, and the cut in the piston rod guide disk extends over 90 degrees of the perimeter of said piston rod guide disk and is engaged by the protrusion on the inner surface of the second part of the syringe.

4. An apparatus according to claim 1, wherein the flange is provided with a set of cuts, a first cut forming a slot through the flange and a pair of second cuts at a position principally diametrically opposite the first cut but provided on both sides of a position exactly diametrically opposite the first cut.

5. An apparatus according to claim 1, wherein the piston rod has a square cross section and is provided with coggings along two opposite sides and is smooth along two other opposite sides.

* * * * *